United States Patent [19]
Villanti et al.

[11] Patent Number: 5,907,062
[45] Date of Patent: May 25, 1999

[54] CONTINUOUS PROCESS FOR THE DINITRATION OF AROMATIC SUBSTRATES

[75] Inventors: Alberto Villanti, Milan; Giacomo Ravetta, Monte Isola, both of Italy

[73] Assignee: Finchimica S.p.A., Manerbio, Italy

[21] Appl. No.: 08/974,104

[22] Filed: Nov. 19, 1997

[30] Foreign Application Priority Data

Dec. 12, 1996 [IT] Italy ................................. TO96A1017

[51] Int. Cl.⁶ ................................................. C07C 209/76
[52] U.S. Cl. ............................................................ 564/411
[58] Field of Search ............................................. 564/411

[56] References Cited

U.S. PATENT DOCUMENTS

| | | |
|---|---|---|
| 2,951,746 | 9/1960 | Kouba et al. .............................. 23/266 |
| 3,694,513 | 9/1972 | Tobey et al. . |
| 3,726,923 | 4/1973 | Foster et al. . |
| 4,621,157 | 11/1986 | McDaniel et al. ....................... 564/411 |
| 4,874,895 | 10/1989 | Donadello ................................ 564/437 |

*Primary Examiner*—Brian M. Burn
*Attorney, Agent, or Firm*—Rothwell, Figg, Ernst & Kurz, P.C.

[57] ABSTRACT

A continuous process for the dinitration of alkyl-substituted derivatives of phenol and aniline, using nitric acid substantially free of sulphuric acid, characterized in which the dinitration is conducted in a single step in a tubular reactor in the presence of a catalytically-effective amount of a catalyst capable of reacting with the nitric acid to form nitrous acid in situ.

12 Claims, No Drawings

CONTINUOUS PROCESS FOR THE DINITRATION OF AROMATIC SUBSTRATES

The present invention concerns a continuous process for the dinitration of aromatic compounds, particularly of dinitratable, substituted derivatives of phenol and aniline.

More specifically, the invention concerns a method for the dinitration of N-alkyl-3,4-dimethyl-benzenamine, in which the alkyl group is preferably 1-ethylpropyl, 1-methylbutyl or sec-butyl, and nitric acid substantially free of sulphuric acid is used as the nitrating agent.

The continuous dinitration of aromatic substrates is known in the technical literature. U.S. Pat. No. 2,951,746 describes continuous nitration in a tubular reactor, although only in relation to toluene as the substrate and using a sulphonitric mixture.

With reference to the nitration of substrates which are active towards electrophilic aromatic substitutions, such as anilines and phenols, U.S. Pat. No. 4,621,157 describes a continuous process conducted in conventional stirred tank reactors, particularly for the production of N-alkyl-2,6-dinitro-3,4-dimethyl-benzenamine, known commercially as Pendimethalin.

The process described therein is conducted in two stages; in the first stage, the alkyl-substituted phenol or aniline derivative is reacted with relatively dilute nitric acid in the presence of an organic, water-immiscible liquid solvent to obtain the mononitro derivative or a nitric acid salt of the starting aniline. In the second stage, the product of the starting aniline. In the second stage, the product of the first stage is further reacted with relatively concentrated nitric acid to obtain the corresponding dinitro derivative. Both stages are conducted in continuous stirred tank reactors (C.S.T.R.) and, in the second, dinitration stage, the residence time is approximately one hour.

According to the present invention, it has been discovered that the dinitration of the aforesaid active aromatic substrates using nitric acid can be achieved in a single stage in a tubular reactor, with residence times of the order of several seconds and with extremely high yields being obtained.

In view of this discovery, the subject of the invention is the continuous dinitration of dinitratable alkyl-substituted derivatives of phenol or aniline using nitric acid as the nitrating agent, characterised in that the reaction is conducted in a tubular reactor in a single stage, a catalytically-effective amount of a catalyst capable of reacting with the nitric acid to form nitrous acid in situ being supplied to the reactor.

It is known that nitrous acid has an anti-catalytic activity in the nitration of aromatic substrates which are not active towards electrophilic attack, while it has a positive catalytic activity in the case of strongly active substrates such as anilines or phenols. Notwithstanding this, in the technical literature relating to the batch or continuous nitration of these strongly active substrates, the presence of nitrous acid as a catalyst, or of compounds capable of generating nitrous acid in situ, is not considered necessary.

By contrast, according to the present invention, it is apparent that the presence of the aforesaid catalysts is essential for the success of the dinitration, in that if the substrate and nitric acid are fed alone in the absence of a catalyst, there is no appreciable evidence of nitration in the mass recovered from the outlet of the reactor. Inorganic salts of nitrous acid, in particular, salts of alkali metals or reducing substances that are easily oxidised by nitric acid such as, for example, aliphatic or aromatic aldehydes, which permit the in situ production of the necessary nitrous acid, are preferably used as catalysts in the invention.

Aliphatic aldehydes comprise aldehydes having a linear or branched alkyl chain with 1 to 12 carbon atoms, preferably from 1 to 3 carbon atoms; acetaldehyde is preferred; aromatic aldehydes comprise benzaldehyde, optionally substituted in the aromatic ring with aliphatic $C_1$–$C_3$ groups or halogens.

The presence of the catalyst triggers the immediate start of the reaction with the result that the substrate is converted quantitatively into the products of dinitration even in the very short residence time within the reactor.

The catalytically-effective amount used can vary within a wide range and is generally between 0.01 to 1.5 parts by weight with reference to 100 parts of aqueous nitric acid.

The dinitration reaction can be conducted in the presence or absence of a solvent. In the case of a solvent reaction, water-immiscible organic solvents in which the aromatic substrate dissolves are preferably used; the preferred solvent, particularly for the production of the dinitroaniline Pendimethalin, is dichloroethane. The concentration of the aromatic substrate in the solvent can vary within a wide range and is generally between 15 and 50% by weight. Concentrated nitric acid which is substantially free of sulphuric acid is used as the dinitrating agent, generally at a concentration of between 20 and 100% by weight; concentrated nitric acid at 45 to 70% by weight is preferably used. The nitric acid is preferably used in stoichiometric excess with respect to the dinitration reaction.

As is known, dinitration reactions are strongly exothermic and, for this reason, are potentially at risk of thermal explosion (run-away). This notwithstanding, the method according to the invention, conducted in a tubular reactor, enables accurate and effective thermal control. The reactor can, in fact, be designed such that it can be immersed in a thermostatic bath, or enclosed in a jacket; the same result can be achieved by conducting the reaction in a tubular heat exchanger used as a reactor. In the preferred embodiment, the reactor is immersed in a thermostatic bath, enabling the reaction temperature to be maintained between 50 and 70° C.

In the preferred embodiment, the feeds of the nitric acid and of the aromatic substrate comprising the catalyst and the solvent, if used, after having passed through a first portion of the tubular reactor, are passed through a tubular, static mixer device, capable of achieving the intimate mixing of the flows, and thereby enabling the rapid completion of the reaction. Static mixers are known and commercially available; for example, static mixers having an internal structure such as those produced by Sulzer Chemtech Limited, or the Kenics Static Mixer sold by Chemineer Limited can be used in the invention. The preferred static mixer is a tubular device having an internal helical structure including back-mixing sections, such as the aforesaid Kenics Static Mixer.

In the preferred embodiment of the process, specifically for the production of Pendimethalin, the dinitration step is conducted at a temperature of between 50 and 90° C. with residence times in the tubular reactor and mixer of around 10–20 seconds. The output stream from the reactor is passed to a phase separator for the separation of the aqueous phase, containing dilute nitric acid, from the immiscible organic phase containing or constituted by the crude dinitration product. The aqueous phase may be fed to a concentration stage for azeotropic distillation to obtain nitric acid at the desired concentration which can then be resupplied directly to the dinitration step.

The advantages of the process according to the invention are:

very short residence times and, consequently, a limited hold-up of the reactor (more than 200 times less than that of a stirred tank reactor of equal productivity);

the easy and accurate control of the reaction temperature by virtue of the on-line heat exchange, the favourable volume/surface ratio, the high linear velocities and the high heat exchange capacity;

a low N-nitroso and N-nitro derivative content in the dinitroanilines produced, which derivatives are inevitably co-produced in the course of dinitroaniline synthesis. By acting correctly and proceeding with the rapid separation of the organic phase from the acid phase, reaction masses are obtained in which the aforesaid N-nitroso derivatives do not exceed 6 to 7% by weight of the total weight of the dinitro derivatives, while the N-nitro derivative content does not exceed 50 to 100 ppm by weight with respect to the total weight of the dinitro derivatives.

The advantages described above also mean that the risk of thermal run-away is greatly reduced and, consequently, the management of the industrial installation is much safer.

In addition, there is a greater economy of investment, less need for maintenance, and reduced energy consumption.

The method according to the invention will be further illustrated by the following non-limitative examples in which a reaction product is subjected to dinitration according to the method described in U.S. Pat. No 4,874,895.

EXAMPLE 1

The dinitration of N-(1-ethylpropyl)-3,4-dimethyl-benzenamine is carried out in a pilot plant in a tubular reactor having a static mixer; the tubular reactor is constituted by a coil in three joined sections, each 5000 mm in length with an internal diameter of 4 mm, with temperature sensors fitted at the junctions between them. The Kenics Static Mixer is a 190 mm long tubular body inserted between the second and third sections. The reactor is immersed in a water-cooled thermostated bath. 67% nitric acid supplemented with 5000 ppm by weight of $NaNO_2$ is fed to the reactor at a rate of 15 l/h at the same time as a solution of 39% by weight N-(1-ethylpropyl)-3,4-dimethyl-benzenamine in dichloroethane; this solution is fed at a rate of 21 l/h. After a period of 15 minutes, during which time the system reaches operating conditions, approximately 6 kg of reaction mass was collected in a separator. After phase separation of the acid phase from the organic phase, this latter which—leaving aside the solvent—is composed of 95% by weight dinitration products and contains 6.8% by weight N-nitroso-N-(1-ethylpropyl)-2,6-dinitro-3,4-dimethyl-benzenamine and 54 ppm p/p N-nitro-N-(1-ethylpropyl)-3,6-dinitro-3,4-dimethyl-benzenamine, is washed and subjected to denitrosation by treatment with aqueous hydrobromic acid and sulphamic acid to transform its N-nitroso derivative co-produced in the course of the reaction into N-(1-ethylpropyl)-2,6-dinitro-3,4-dimethyl-benzenamine. Once the solvent is evaporated, 1.78 kg of crude N-(1-ethylpropyl)-2,6-dinitro-3,4-dimethyl-benzenamine were obtained with a titre of 94.2%.

EXAMPLE 2

As for example 1 except that 1500 ppm benzaldehyde is added to the solution of N-(1-ethylpropyl)-3,4,-dimethyl-benzeneamine in dichloroethane instead of adding sodium nitrite to nitric acid. 1.77 kg of crude product is obtained, being 94.3% by weight dinitration products and containing 7.3% by weight N-nitroso-N-(1-ethylpropyl)-2,6-dinitro-3, 4-dimethyl-benzenamine and 38 ppm p/p N-nitro-N-(1-ethylpropyl)-2,6-dinitro-3,4-dimethyl-benzenamine. At the end of the treatment, a product having a titre of 93.9% in N-(1-ethylpropyl)-2,6-dinitro-3,4-dimethyl-benzenamine is obtained.

EXAMPLE 3

60% nitric acid supplemented with 1600 ppm $NaNO_2$ is fed to the reactor at a rate of 28 l/h, together with N-(1-ethylpropyl)-3,4-dimethyl-benzenamine at a rate of 7.5 l/h. After a period of 20 minutes during which the system reaches operating conditions, approximately 5 kg of reaction mass are collected in a thermostated separator at 70° C. containing 13 kg of water at the same temperature. After discarding the aqueous acid phase, the fused organic phase is washed twice with 6 l water heated to 70° C., and analysed. It contains 5.9% by weight of N-nitroso-N-(1-ethylpropyl)-2,6-dinitro-3,4-dimenthyl-benzenamine.

Subjected to denitrosation by means of treatment with aqueous hydrobromic acid and sulphamic acid, the resulting mass contains 96.8% Pendimethalin.

What is claimed is:

1. A continuous process of dinitration of N-alkyl-3,4-dimethyl-benzenamines wherein said alkyl is selected from the group consisting of 1-ethylpropyl, 1-methylbutyl and sec-butyl, using nitric acid substantially free of sulphuric acid, comprising a single dinitration step conducted in a tubular reactor in the presence of a catalytically-effective quantity of a catalyst which reacts with the nitric acid to form nitrous acid in situ.

2. The process of claim 1, wherein said catalyst is selected from the group comprising the alkali metal nitrites and the aldehydes.

3. The process of claim 2, wherein the catalyst is an alkali metal nitrite used at a concentration of 50–10,000 ppm by weight with reference to the nitric acid.

4. The process of claim 1, wherein the reaction is conducted in a water-immiscible organic solvent.

5. The process of claim 1, wherein the reaction is conducted in the absence of a solvent.

6. The process of claim 1, wherein the nitric acid is used at a concentration of 20 to 100% by weight.

7. The process of claim 6, wherein the nitric acid is at a concentration of 45 to 70% by weight.

8. The process of claim 1, wherein a static tubular mixer is located at the start of the tubular reactor.

9. The process of claim 1, wherein a static tubular mixer is between two consecutive sections of the same tubular reactor.

10. The process of claim 1, wherein the said alkyl-substituted aniline is N-(1-ethylpropyl)-3,4-dimethyl-benzeneamine.

11. The process of claim 2, wherein the catalyst is an aldehyde used at a concentration of 50–10,000 ppm by weight with reference to said N-alkyl-3,4-dimethyl-benzenamine.

12. The process of claim 11 wherein said N-alkyl-3,4-dimethyl-benzenamine is N-(1-ethylpropyl)-3,4-dimethyl-benzenamine.

* * * * *